United States Patent
Joseph

(10) Patent No.: US 6,238,671 B1
(45) Date of Patent: May 29, 2001

(54) PROCESS FOR THE GENTLE RECOVERY OF EXTRACT FRACTIONS FROM HYPERICUM, PHARMACEUTICAL PREPARATIONS CONTAINING THE SAME AND THEIR USE

(75) Inventor: Heinz Walter Joseph, Berg (DE)

(73) Assignee: Bionorica Arzneimittel GmbH, Neumarkt (DE)

( * ) Notice: Subject to any disclaimer, the term of this patent is extended or adjusted under 35 U.S.C. 154(b) by 0 days.

(21) Appl. No.: 09/292,162

(22) Filed: Apr. 15, 1999

(30) Foreign Application Priority Data

Apr. 22, 1998 (DE) .............................. 198 18 001

(51) Int. Cl.⁷ .......................... A61K 35/78; A61K 31/05; A01N 31/08
(52) U.S. Cl. ................. 424/195.1; 514/732; 514/738
(58) Field of Search ................ 424/195.1; 514/732, 514/738

(56) References Cited

U.S. PATENT DOCUMENTS

| | | | |
|---|---|---|---|
| 4,898,891 | * | 2/1990 | Lavie et al. . |
| 5,120,412 | * | 6/1992 | Mazur et al. . |

FOREIGN PATENT DOCUMENTS

| | | | |
|---|---|---|---|
| 1569849 | * | 4/1975 | (DE) . |
| 3935772 | * | 4/1991 | (DE) . |
| 42 39 959 | | 6/1994 | (DE) . |
| 196 19 512 | | 7/1997 | (DE) . |
| 196 46 977 | | 1/1998 | (DE) . |
| 0 256 452 | | 2/1988 | (EP) . |
| 0 599 307 | | 6/1994 | (EP) . |
| 2117778 | * | 7/1972 | (FR) . |
| 2101888 | * | 1/1983 | (GB) . |
| 5 255 046 | | 10/1993 | (JP) . |
| 9157151 | * | 12/1995 | (JP) . |

OTHER PUBLICATIONS

Pavia et al. Intro. to Organic Laboratory Techniques. Saunders College Publ., pp. 500–501, 1982.*
Meier, B. The extraction strength of enthanol/water mixtures commonly used for the processing of herbal drugs. Planta Med. vol. 57, No. 8, Supplement, Dec. 1991, pp. A26–A27.
German Search Report w/English Translation of Form PCT-ASA-210.

* cited by examiner

Primary Examiner—Christopher R. Tate
(74) Attorney, Agent, or Firm—Ratner & Prestia

(57) ABSTRACT

A method of preparing an extract fraction of *Hypericum perforatum* L by preparing an aqueous ethanolic extract of *Hypericum perforatum* L, concentrating the extract to a predetermined degree by evaporation thus forming a precipitate and a supernatant, repeating the concentrating and separating steps at least once with the supernatant, optionally redissolving the separated precipitate obtained in a previous step and obtaining a product extract of *Hypericum perforatum* L from one of the supernatant or the precipitate of the step wherein the precipitate and supernatant are formed or the redissolved precipitate of the proceeding step.

6 Claims, No Drawings

PROCESS FOR THE GENTLE RECOVERY OF EXTRACT FRACTIONS FROM HYPERICUM, PHARMACEUTICAL PREPARATIONS CONTAINING THE SAME AND THEIR USE

The present invention relates to a process for the gentle recovery of extract fractions of Hypericum (St. John's wort) having a high portion of active and/or standard substances, pharmaceutical preparations containing the same and their use for the therapy of depression.

St. John's wort, *Hypericum perforatum* L., is a plant drug which has been used for a long time for treating psycho-vegetative disorders (Daunderer, "Klinische Toxikologie", 81, Suppl. March 1994). In addition, *Hypericum perforatum* is used to treat photosensitive dermatoses, functional and arteriosclerotic depression, conditions after *Commotio cerebri* and *Commotio spinalis* (Roth, Daunderer "Giftliste" (List of Toxic Substances), 60, Suppl. October 1994). *Oleum hyperici* is used to treat burns and wounds. The antimicrobial activity of hypericum against staphylococci and streptococci (Roth, Daunderer, see above) or viruses (EP-A-0 256 452) is also known. The dried leaves collected just before or during bloom or aqueous or alcoholic—especially ethanolic—full extracts or full dry extracts are used as a drug, for example Helarium® Hypericum.

In detail, about fifteen active ingredients have been isolated from hypericum, the most important of which are hypericin, pseudohypericin, hyperforin, a prenylated phloroglucin, adhyperforin and hyperosid.

So far, the anti-depressive effect has been attributed to hypericin as the active ingredient which determines effectiveness (cf. Roth, Daunderer as above; Daunderer, as above). It was assumed that the mechanism of action is based on the inhibition of MAO (monoamino oxidase) or COMT (catechol-O-methyl transferase). Since no such effect was confirmed upon administration of free hypericin, a dispute has arisen in literature whether the effect may not be due to hyperforin as an additional active ingredient after all (cf. EP-A-0 599 307, for example).

So far, full dry extracts of hypericum and a dry extract enriched in hyperforin and produced according to the process of EP-A-0 599 307 have been available commercially. With regard to effect, all these preparations are equivalent to tricyclic anti-depressive drugs, but have considerably reduced side effects, especially with regard to tolerance, reaction speed, fatigue and the ability to drive. In comparison with tricyclic anti-depressive drugs, they therefore constitute a far more easily tolerable therapeutic agent with the same effect. Patient compliance with this product is far better.

Hypericum extracts containing hypericin and/or hyperforin or the relevant dry extracts may be prepared by various known work-up processes and drying methods. As a rule, such processes start from the full extract the composition of which is determined by the selected starting material. Control of the content of the substance is therefore determined by the selection of suitable plants or the work-up method, e.g. the selection of the extractant, since hyperforin is very sensitive and decomposes easily. Hypericin as a pure substance is obtained in accordance with DE-B-15 69 849, for example.

Unfortunately, it is not possible with prior art processes such as pure solvent extraction (DE-B-15 69 849, or DE-C-39 35 772) and two-stage extraction (EP-A-0 599 307) to recover extracts containing hypericin and/or hyperforin with a defined and adjustable content of active ingredient. Especially in order to prepare hypericin-containing extracts, the method of lipophilic extraction is used. These lipophilic extracts can be recovered by using suitable solvents (methanol, acetone, methyl ethyl ketone). In order to recover hyperforin-containing extracts, it is possible to first prepare aqueous or hydrophilic extracts which are then washed with lipophilic solvents such as DMSO or dioxane or subjected to a lipophilic solids extraction, for example on PVP or active carbon (EP-A-0 599 397 or EP-A-0 702 957).

It is a disadvantage of these processes that the more lipophilic solvent must be replaced by a solvent which is suitable for pharmaceutical applications and the recovery of the extract requires a two-stage process. In addition, varying ingredient spectres result from the variance of the plants with regard to the content of the active ingredients which may not be controlled freely, but depend on the total content of active ingredients. When preparing dry extracts according to the prior art, it is therefore not possible to control the active ingredients. This would only be permitted by selecting an additional solvent or selecting the starting plant material accordingly.

In case of the well-known simple ethanolic dry full extracts which are prepared by means of spray drying and conventional vacuum drying, it is not possible either to influence the spectrum of the contents, because the dry extract or the dry extract preparation contains all the original ingredients extracted beforehand. Controlling the spectrum of active ingredients is only possible by selecting suitable plants.

Therefore, it was the object of the invention to develop a simple and gentle extraction process, which may be controlled with regard to the content of the active ingredients (hypericin and/or hyperforin) and permits the preparation of extracts the hyperforin and hypericin contents of which are clearly defined and adjustable.

This object is solved by a process for recovering extract fractions of *Hypericum perforatum* L. comprising
a) preparing an aqueous ethanolic extract of *Hypericum perforatum* L. by known methods,
b) concentrating the extract to a predetermined degree and
c) separating the precipitate obtained in step b) from the supernatant,
steps b) and c) being repeated at least once with any supernatant from step c).

The extractant for recovery of the aqueous ethanolic extract in step a) has an ethanol content of at least 40% by volume, preferably 60 to 90% by volume and most preferably 80% by volume.

Preferably, steps b) and c) are repeated at least once, more preferably twice to four times and most preferably twice. As a result, at least 2, preferably 2 to 4 or 5 and most preferably 3 or 4 extract fractions are obtained, the higher number of extract fractions being obtained, if the concentration in step b) in the last series of steps b)/c) is not carried out to 100% so that a (residual) supernatant is obtained in addition to the precipitate.

In a preferred embodiment, the process comprises an additional step d) wherein the precipitate obtained in step c) is redissolved. Redissolution is preferably carried out in a water/ethanol mixture having a higher ethanol content than the original extractant, for example a mixing ratio of ethanol/water from 95 to 50/5 to 50, more preferably 90 to 80/20 to 10 (v/v). To refine the separation, the redissolved precipitates may once again be subjected to one or several series of steps b) to d) and thus refractionated.

Preferably, precipitates or fractions are recovered which have degrees of concentration (calculated as amount of redistillation product (g): starting amount (g)) of 0 to 40–50%, 40–50 to 60–75% and 60–75 to 100%. If a finer separation is desired, it goes without saying that additional fractions corresponding to degrees of concentration of 0–40%, 40–50%, 50–65%, 65–75% and 75–85% may be collected. Additional separation steps are also feasible.

Owing to its more lipophilic character, hyperforin first precipitates at degrees of concentration of approx. 50% upon thickening by evaporation or concentration while hypericin as the more hydrophilic substance remains in solution up to a degree of concentration of approx. 50%. Above degrees of concentration of approx. 50%, the hypericin content of the precipitate rises significantly, and fractions in the precipitate enriched in hypericin in comparison with the full extract are obtained at degrees of concentration of 80 to 85%. In comparison, the precipitate initially obtained is enriched in hyperforin in comparison with the full extract.

Therefore, it is possible to obtain drugs enriched or depleted in hyperforin and hypericin, respectively, by selecting the pertinent degrees of concentration and dividing fractionation and, optionally, by redissolution and refractionation. The degree of enrichment and thus the content of the active ingredient may be freely adjusted in the process according to the invention.

Another advantage of the process according to the invention lies in the fact that only one extractant complying with legal requirements is required, namely an aqueous ethanolic solution. Additional, more lipophilic extractants such as acetic acid ethyl ester, acetone, methyl ethyl ketone or chlorinated hydrocarbons need not be used nor are lipophilic solid extraction steps required which use, for example, active carbon or PVP. Since additional solvents and extractants can be avoided, economic and ecological advantages also result. In addition, the ethanol withdrawn during extraction or the withdrawn ethanol/water mixture may be recycled and fed back into the process resulting in considerable savings concerning the extractant.

Owing to the gentle concentration by evaporation/fractionation, decomposition of the more sensitive hyperforin is substantially avoided which constitutes another advantage vis-à-vis the prior art.

Contamination of the fluid extract by lipophilic or hydrophilic solvents as mentioned above can also be avoided, just as other extraction or chromatographic work-ups. Subsequent work-up steps can be carried out with fewer or different materials. The most important advantage, however, lies in the fact that the present gentle process permits controlling the content of the relevant active ingredients in the extracts. This was not possible until now.

Concentration or fractionation in steps b) and c) may be carried out with the aid of any device, for example a rotational evaporator which permits accurate control of the degree of concentration. For example, it can be carried out by means of an Inox Glatt® apparatus, such as the Inox-Glatt dryer systems IUT 20, IUT 50, IUT 100 or IUT 2000.

Drying is carried out at a starting temperature between 150 to 100° C., preferably 120° C., and a return temperature between 20 and 1° C., preferably 5° C., respectively, an interior temperature between 10 and 80° C., preferably 25 to 70° C., and a pressure between 0.5 and 1,000 mbar, preferably 5 to 100 mbar, most preferably 30 to 70 mbar. For drying, the agitator speed is adjusted to a speed between 0 and 10 rpm, preferably between 0 to 5 rpm and the chopper speed between 200 and 800 rpm.

At the beginning of concentration, care must be taken that the lipophilic medium—ethanol in the present case—is withdrawn at the predetermined starting and return temperature, an interior temperature between 10 and 80° C. and a vapour temperature between 15 and 65° C., preferably 25 to 55° C.

Using the preparation of hypericum dry extracts as an example, it has been possible to show that a far higher total content of all extract fractions of hyperforin or hypericin, respectively, could be obtained. This finding was highly surprising since no difference occurred in the area of the extractant used concerning the lipophilic behaviour of the compounds and the threshold concentrations obtained dissolved easily in the present extractant.

By treating the liquid extracts with the process according to the invention, the inventors have also succeeded in arbitrarily adjusting the contents of the active ingredient which had not been possible so far, and the most gentle concentration of dry extracts with defined high contents of standard or active ingredients from drugs produced with a certain ethanol/water concentration. Owing to the defined content of the active ingredient, the work-up of the extract fraction is also simplified.

The physical work-up of all other known drying processes results in dry extracts which are less easy to control and which have a fixed content of the active ingredient. This may diminish a possible therapeutic success.

The gentle recovery of solvents which may be used again is another ecologically advantageous aspect of this process. Finally, it is an unexpected advantage that the extract fractions obtained may be subjected to further concentration or fractionation to obtain valuable natural substances.

The product precipitates or supernatants may be processed to finished pharmaceutical preparations or semi-manufactured products. This may take place in the same drying apparatus and in the enriched form.

The pharmaceutical preparations may be provided in forms suitable for oral and parenteral application, for example in the form of solutions, especially tinctures or solutions for drinking, suspensions, capsules, sugar-coated tablets, tablets, suppositories etc., and may contain suitable pharmaceutical excipients and carriers such as fillers, granulation aids, sweeteners, flavours, preservatives etc.

The pharmaceutical preparations containing extract fractions enriched with regard to both hyperforin and hypericin are preferably used to treat depression, but may also be used for additional indications known for hypericum.

The following example has the purpose to illustrate, but not to limit the invention.

EXAMPLE

Various batches of hypericum tincture (60/40EtOH/$H_2O$ mixture) were used to prepare the extract fractions. In the starting solutions, the total content of active ingredients in the dry extract and the hypericin content were determined according to DAC and a total spectrum prepared by HPLC. The compounds of interest were measured and separated at the individual concentration stages. Several experiments were carried out for the process according to the invention, with the amount of the tinctures/fluid extracts varying between 50 and 1,000 liters. The tinctures were sucked into the Inox-Glatt® vacuum dryer at room temperature and dried at 120° C. starting temperature and 5° C. return temperature.

The evaporation output was between 300 and 330 l/hr. It is subject to variations owing to the amount of alcohol which distils more easily at the beginning in comparison with the less volatile water. The interior temperature was 30 to 40° C. and the vapour temperature 30 to 40° C. The pressure was below 120 mbar.

TABLE 1a

| Degree of concentration in % | Spec. hypericin in % | Spec. hyperforin in % |
|---|---|---|
| 0 | 0.58 | 0.74 |
| 24.7 | 0.26 | 1.6 |
| 32.5 | 0.30 | 1.5 |
| 48.9 | 0.40 | 20.4 |
| 57.9 | 0.73 | 7.1 |
| 66.8 | 1.06 | 1.2 |
| 86.4 | 0.53 | n.d. |

TABLE 1b

| Degree of concentration in % | Spec. hypericin in % (precipitates) | Spec. hyperforin in % (precipitates) |
|---|---|---|
| 0 | 0.52 | 0.74 |
| 32 | 0.25 | 1.6 |
| 49 | 0.40 | 6.1 |
| 59 | 0.73 | 7.4 |
| 67 | 0.78 | 6.1 |
| 76 | 0.94 | 0.4 |
| 85 | 0.83 | 0.4 |
| 94 | 0.48 | n.d. |

As shown by the above tables, a higher initial hyperforin content is found in the precipitate obtained by the process according to the invention as compared to complete drying. After removal of the supernatant, this precipitate may be dissolved in 90% ethanol, removed from the container and used as required. The supernatant which is to be pumped back may be concentrated further and, after further concentration, the precipitates show a higher content of hydrophilic substances, especially hypericin.

What is claimed is:

1. An extract fraction of *Hypericum perforatum* L, obtained by the process comprising
    a) preparing an aqueous ethanolic extract of *Hypericum perforatum* L.;
    b) concentrating the extract to a predetermined degree by evaporation whereby a precipitate and supernatant is formed;
    c) separating the precipitate from the supernatant;
    d) repeating steps b) and c) at least once with the supernatant from step c)
    e) optionally redissolving the separated precipitate obtained in step (c); and
    f) obtaining a product extract of *Hypericum perforatum* L from one of the supernatant or the precipitate of step c) or the redissolved precipitate of step e).

2. An extract fraction according to claim 1, being one of the precipitate or the redissolved precipitate of the first step c) or d) respectively, concentrated to 40 to 50% of the original extract volume in step b).

3. An extract fraction according to claim 1, being one of the precipitate of step d) after a third repetition of steps b) and c) or the precipitate of step d) after a third repetition of steps b) and c) redissolved in step e), in which third step d), the concentration of the extract being from 60 to 100% of the original extract volume.

4. A pharmaceutical preparation comprising an extract fraction, said extract fraction obtained by the process comprising
    a) preparing an aqueous ethanolic extract of *Hypericum perforatum* L.;
    b) concentrating the extract to a predetermined degree by evaporation whereby a precipitate and supernatant is formed;
    c) separating the precipitate from the supernatant; and
    d) repeating steps b) and c) at least once with the supernatant from step c)
    e) optionally redissolving the separated precipitate obtained in step (c); and
    f) obtaining a product extract of *Hypericum perforatum* L from one of the supernatant or the precipitate of step d) or the redissolved precipitate of step e).

5. A pharmaceutical preparation according to claim 4 comprising an extract fraction enriched in hypericin, said extract fraction being one of the precipitate of step d) after a third repetition of steps b) and c) or a precipitate of step d) after a third repetition of steps b) and c) redissolved according to step e in which the concentration of the extract in step d) is from 60 to 75% of the original extract volume.

6. A pharmaceutical preparation according to claim 4, containing an extract fraction enriched in hypoforin said extract fraction being one of the precipitate of step d) or the redissolved precipitate of step e) concentrated to between 40% and 50% of the original extract volume of step b).

* * * * *